(12) United States Patent
Frank et al.

(10) Patent No.: US 9,630,890 B2
(45) Date of Patent: Apr. 25, 2017

(54) REACTIVE CHROMATOGRAPHY PROCESS FOR EQUILIBRIUM-LIMITED REACTIONS

(71) Applicant: Dow Global Technologies LLC, Midland, MI (US)

(72) Inventors: Timothy C. Frank, Midland, MI (US); Megan E. Donaldson, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/888,512

(22) PCT Filed: May 2, 2014

(86) PCT No.: PCT/US2014/036602
§ 371 (c)(1),
(2) Date: Nov. 2, 2015

(87) PCT Pub. No.: WO2014/179706
PCT Pub. Date: Nov. 6, 2014

(65) Prior Publication Data
US 2016/0145167 A1    May 26, 2016

Related U.S. Application Data

(60) Provisional application No. 61/819,245, filed on May 3, 2013.

(51) Int. Cl.
| | | |
|---|---|---|
| C07C 67/03 | (2006.01) | |
| C07B 41/00 | (2006.01) | |
| C07B 41/12 | (2006.01) | |
| B01D 15/36 | (2006.01) | |
| B01D 15/18 | (2006.01) | |
| B01D 15/38 | (2006.01) | |
| C07B 41/02 | (2006.01) | |
| C07C 29/128 | (2006.01) | |

(52) U.S. Cl.
CPC .......... *C07B 41/12* (2013.01); *B01D 15/1821* (2013.01); *B01D 15/1857* (2013.01); *B01D 15/363* (2013.01); *B01D 15/3857* (2013.01); *C07B 41/02* (2013.01); *C07C 29/1285* (2013.01); *C07C 67/03* (2013.01); *Y02P 20/127* (2015.11)

(58) Field of Classification Search
CPC ............................... C07C 67/03; C07B 41/12
USPC .................................................... 560/234, 265
See application file for complete search history.

(56) References Cited

U.S. PATENT DOCUMENTS

| | | |
|---|---|---|
| 3,700,726 A | 10/1972 | Johnson, Jr. et al. |
| 5,405,992 A | 4/1995 | Funk et al. |
| 6,444,842 B1 | 9/2002 | Gerberich et al. |

FOREIGN PATENT DOCUMENTS

| | | |
|---|---|---|
| CN | 102992956 | 3/2013 |
| EP | 0849254 | 6/1998 |

OTHER PUBLICATIONS

F. Lode, et al., "Continuous Reactive Chromatography" Chemical Engineering Science, 56 (2001) 269-291 (24 pgs).
International Search Report & Written Opinion for related PCT Application PCT/US2014/036602, mailed Nov. 19, 2014 (72 pgs).
International Preliminary Report on Patentability for related PCT Application PCT/US2014/036602, mailed Jul. 16, 2015 (15 pgs).

*Primary Examiner* — Sikarl Witherspoon
(74) *Attorney, Agent, or Firm* — Brooks, Cameron & Huebsch, PLLC (57) ABSTRACT

The present disclosure provides for a process for an equilibrium limited reaction using reactive chromatography unit (RCU) in which a first organic donor reactant (FODR) and a second organic acceptor reactant (SOAR) react to form a product mixture of a first acceptor product (FAP) and a second donor co-product (SDCP). The equilibrium-limited reaction does not produce water. The RCU has separation media to separate the product mixture into a raffinate and an extract. The FODR is in a stoichiometric deficit relative to the SOAR for the equilibrium limited reaction, so that the SOAR acts as the eluent for both the raffinate and the extract, and so as not to produce an azeotrope of FODR and the SDCP in the extract.

14 Claims, 3 Drawing Sheets

REACTIVE CHROMATOGRAPHY PROCESS FOR EQUILIBRIUM-LIMITED REACTIONS

This application is a National Stage Application under 35 U.S.C. §371 of International Application No. PCT/US2014/036602, filed May 2, 2014 and published as WO 2014/179706 on Nov. 6, 2014, which claims the benefit to U.S. Provisional Application 61/819,245, filed May 3, 2013, the entire contents of which are incorporated herein by reference in its entirety.

FIELD OF THE DISCLOSURE

The present disclosure relates generally to a process for an equilibrium limited reaction of a first organic donor reactant (FODR) with a second organic acceptor reactant (SOAR) to form a first acceptor product (FAP) and a second donor co-product (SDCP) without producing water as a reaction product.

BACKGROUND

An acylation reaction introduces an acyl functional group (R—C(=O)—) into a chemical compound by reaction with an acylating agent or acyl donor. Reactions of this type include transesterification of hydroxy compounds with esters to form a new ester plus co-product alcohol, and amidation of amines with esters to form amides plus co-product alcohol. For example, in the reaction of an alcohol with an acetate ester acylating agent, the acylating agent replaces the hydrogen atom of the alcohol hydroxyl group with an acetate group. Reactions similar to acylation include transamidation of amines with amides and transamination of ketones with amines. Alkyl acetates, such as methyl acetate and ethyl acetate, are commonly used acylating agents used to add an acetate functional group to organic compounds containing a hydroxyl group such as, for example, glycol ethers. This reaction of methyl acetate or ethyl acetate with the glycol ether is also known as transesterification. Transesterification is a reaction between an ester of one alcohol and a second alcohol to form an ester of the second alcohol and an alcohol from the original ester. The transesterification of methyl acetate, an ester of methanol, is of particular interest due to its relative abundance as a side product from the production of polyvinyl alcohol.

Acylation reactions (and similar reactions such as transamidation and transamination) commonly are limited by chemical equilibrium such that product and/or co-product must be removed from the reaction mixture to drive conversion to high levels needed for commercially feasible application. A well-known method of achieving this is to combine reaction with distillation in a reactive distillation operation. In reactive distillation, the transesterification reaction takes place in the distillation apparatus that is used to separate the products from the reaction mixture. This technique is especially useful for equilibrium-limited reactions, such as transesterification reactions. Conversion can be increased beyond what is expected by the equilibrium due to the continuous removal of reaction products from the reactive zone in the distillation apparatus. However, the use of reactive distillation often is complicated by the formation of azeotropic mixtures that are difficult to separate using distillation methods. As such, there is a need in the art for a process that can drive equilibrium limited reactions (e.g. acylation reactions) without needing to distill azeotropic mixtures.

SUMMARY

The present disclosure provides for a process for an equilibrium limited reaction of a first organic donor reactant (FODR) with a second organic acceptor reactant (SOAR) to form a first acceptor product (FAP) and a second donor co-product (SDCP) without producing water as a reaction product. As water is not produced, issues arising from the formation of an aqueous azeotrope are not present. In other words, as water is not a byproduct of the reaction an azeotrope of organic components with water cannot be formed. The process allows for an equilibrium limited reaction of a SOAR with a FODR at a predetermined temperature to form the FAP and the SDCP at commercially attractive conversion levels.

The process includes supplying the FODR and the SOAR to a reactive chromatography unit (RCU) to create a reaction mixture, where the FODR is in a stoichiometric deficit relative to the SOAR for the equilibrium limited reaction. The RCU has separation media to separate a product mixture of the FAP and the SDCP. The FODR in the stoichiometric deficit relative to the SOAR in the reaction mixture reacts at the predetermined temperature in the RCU to form the product mixture that includes the FAP and the SDCP via the equilibrium limited reaction. The product mixture is separated into a raffinate that includes the FAP and an extract that contains the SDCP. The equilibrium-limited reaction is a reversible reaction having an equilibrium conversion value ($X_e$) for the predetermined temperature. Separating the product mixture produces a conversion value for the equilibrium limited reaction that is greater than the equilibrium conversion value for the predetermined temperature. So, the present disclosure helps to achieve a conversion that is greater than the equilibrium conversion value by separating and removing the reaction products, thereby driving the conversion of the reactants. For the various embodiments, the SOAR acts as an eluent for both the raffinate and the extract of the RCU (e.g., both the raffinate and the extract include SOAR). The RCU can be operated in such a manner, as discussed herein, that a single pass conversion of the FODR is from 70 percent (%) to 99%. As this conversion of the FODR is less than 100%, there will be residual unreacted FODR in the product mixture. Upon separation, the raffinate includes the residual unreacted FODR, the SOAR and the FAP, while the extract includes the SOAR and the SDCP.

The raffinate can be further separated into a FAP product fraction and a recycle fraction, where the recycle fraction contains the SOAR, the residual unreacted FODR, and a FAP cut. The recycle fraction is returned to the RCU for the equilibrium limited reaction. The extract can also be separated into at least a SOAR fraction and a SDCP fraction. The SOAR fraction can be returned to the RCU for the equilibrium limited reaction with the FODR. By returning the residual unreacted FODR to the RCU a higher overall conversion of the FODR can be achieved. Such an overall conversion for the FODR can approach 100% overall conversion of the FODR.

The embodiments of the present disclosure can be used for acylation reactions, such as a transesterification reaction. For example, the present disclosure includes the process in which the FODR is an acetate ester and the SOAR is a hydroxy containing organic compound (HCOC) that reacts with the acetate ester to form an organic acetate (OA) and an alcohol co-product (AC) during the equilibrium limited reaction. The acetate ester is in the stoichiometric deficit relative to the HCOC in the RCU that contains a catalyst for the equilibrium limited reaction and the separation media to separate the OA and the AC. The raffinate separated with the separation media contains at least the OA and residual unreacted acetate ester, and the extract separated with the separation media contains at least the AC. Other examples of equilibrium limited reactions include transamination reactions and transamidation reactions.

Among other configurations, the RCU is a simulated-moving bed unit.

DETAILED DESCRIPTION

The present disclosure provides a process for conducting an equilibrium-limited reaction that can avoid separation difficulties seen in reactive distillation based processes (e.g., the formation of an azeotrope that can impact product and/or byproduct removal and thereby limit potential improvements to the equilibrium-limited conversion). Specifically, the process is for the equilibrium limited reaction of a first organic donor reactant (FODR) with a second organic acceptor reactant (SOAR) to form a first acceptor product (FAP) and a second donor co-product (SDCP) without producing water as a reaction product. As water is not produced, issues arising from the formation of an aqueous azeotrope are not present.

The process of the present disclosure uses reactive chromatography for both the equilibrium-limited reaction and the separation of the products, which produces a conversion value for the equilibrium limited reaction that is greater than the equilibrium conversion value for a given predetermined temperature. The process allows for the equilibrium limited reaction of the SOAR with the FODR at the predetermined temperature to form the FAP and the SDCP at commercially attractive conversion levels. The equilibrium-limited reaction is a reversible reaction having an equilibrium conversion value ($X_e$) for the predetermined temperature. The process includes supplying the FODR and the SOAR to a reactive chromatography unit (RCU) to create a reaction mixture, where the FODR is in a stoichiometric deficit relative to the SOAR for the equilibrium limited reaction. The RCU of the present disclosure is a constant volume system.

The RCU has separation media to separate a product mixture of the FAP and the SDCP. The FODR in the stoichiometric deficit relative to the SOAR in the reaction mixture reacts at the predetermined temperature in the RCU to form the product mixture that includes the FAP and the SDCP via the equilibrium limited reaction. The product mixture is separated into a raffinate that includes the FAP and an extract that contains the SDCP. Separating the product mixture produces a conversion value for the equilibrium limited reaction that is greater than the equilibrium conversion value for the predetermined temperature. So, the present disclosure helps to achieve a conversion that is greater than the equilibrium conversion value by separating and removing the reaction products, thereby driving the conversion of the reactants.

For the various embodiments, the SOAR acts as an eluent for both the raffinate and the extract of the RCU (e.g., both the raffinate and the extract can include SOAR). The RCU can be operated in such a manner that a single pass conversion of the FODR is from 70 percent (%) to 99%. As this conversion of the FODR is less than 100%, there will be residual unreacted FODR in the product mixture. Upon separation, the raffinate includes the residual unreacted FODR, the SOAR and the FAP, while the extract includes the SOAR and the SDCP. An azeotrope of the SDCP and the residual unreacted FODR is avoided; however, as the SDCP is present in the extract while the residual unreacted FODR is present in the raffinate.

The process of the present disclosure uses a reactive chromatography unit (RCU) for the equilibrium limited reaction of the FODR with the SOAR in the reaction mixture to form the FAP and the SDCP in the product mixture. As discussed herein, the RCU allows for the equilibrium limited reaction of the FODR and the SOAR in the reaction mixture and the separation of the FAP and the SDCP in the product mixture to drive the conversion of the equilibrium-limited reaction. In addition, the separation of the residual unreacted FODR in the raffinate from the SDCP in the extract by the RCU helps the process avoid the formation of an azeotrope in the reaction products emerging from the RCU.

As used herein, the organic donor reactant is an organic compound containing a functional group that during the equilibrium reaction leaves that compound and transfers to become part of an acceptor compound. An example is the donation and transfer of an acetate group from an organic donor reactant to an acceptor compound which then contains the acetate group. Other examples of organic donor compounds include compounds with amine groups and compounds with amide groups.

The process of the present disclosure includes supplying to the RCU the FODR and the SOAR to create the reaction mixture, where the FODR is in a stoichiometric deficit relative to the SOAR for the equilibrium limited reaction. The FODR in the stoichiometric deficit relative to the SOAR reacts at a predetermined temperature in the RCU to form a product mixture comprising the FAP and the SDCP via the equilibrium-limited reaction. The RCU has separation media to separate the product mixture (e.g., the FAP and the SDCP) into one of two streams: a raffinate and an extract. As the FODR supplied to the RCU is in a stoichiometric deficit relative to the SOAR, the SOAR supplied to the RCU is in a stoichiometric excess relative to the FODR. Due to this stoichiometric excess the SOAR in addition to being a reactant in the equilibrium-limited reaction also acts as the eluent or desorbent (the chromatography elution solvent or mobile phase) for the extract and the raffinate of the RCU. Likewise, because the FODR supplied to the RCU is in the stoichiometric deficit relative to the SOAR, the FODR in the RCU reacts at a predetermined temperature to form the FAP and the SDCP via the equilibrium-limited reaction.

As discussed herein, upon separation the raffinate includes the residual unreacted FODR, the SOAR and the FAP, while the extract includes the SOAR and the SDCP. The raffinate can be further separated into a FAP product fraction and a recycle fraction, where the recycle fraction contains the SOAR, the residual unreacted FODR, and a FAP cut. The recycle fraction is returned to the RCU for the equilibrium limited reaction. The extract can also be separated into at least a SOAR fraction and a SDCP fraction. The SOAR fraction can be returned to the RCU for the equilibrium limited reaction with the FODR. By returning the residual unreacted FODR to the RCU a higher overall conversion of the FODR can be achieved. Such an overall conversion for the FODR can approach 100%. The result is the process of the present disclosure which greatly simplifies the equilibrium-limited reaction process compared to reactive distillation processes, which can have difficulty stripping the SDCP to drive conversion without also taking some of the FODR overhead, thus requiring an additional unit operation to separate the resulting azeotropic mixture of FODR and SDCP.

In an additional embodiment, the FODR in the stoichiometric deficit relative to the SOAR in the RCU can react towards extinction in a single pass of the reactants through the RCU. For example, the FODR in the stoichiometric deficit relative to the SOAR in the RCU can react essentially to extinction (e.g., essentially 100% conversion of the FODR) in a single pass of the reactants through the RCU. For this embodiment, as the FODR reacts towards extinction the process of the present disclosure can avoid the need to separate the FODR from the SDCP, in particular avoiding the difficulties involved in separating an azeotrope that can form from mixtures of the FODR and the SDCP. In an additional embodiment, it is possible that the SOAR is in a stoichiometric deficit relative to the FODR for the equilibrium limited reaction in the RCU. Such embodiments can address certain equilibrium-limited reactions that have the potential of forming an azeotrope of either FAP and SOAR or SDCP and SOAR.

As used herein, an "equilibrium constant" is an value that expresses the relationship between products and reactants of a reversible reaction at equilibrium at a given temperature with respect to a specific unit.

As used herein, an "equilibrium conversion" is the highest conversion ($X_e$) that can be achieved in a reversible reaction at a given temperature (e.g., an isothermal reaction temperature) for a constant volume system.

The process of the present disclosure uses the RCU as both a reaction vessel and a chromatography unit. The RCU allows for the simultaneous reaction of reactants and separation of products for reversible reactions (e.g., an equilibrium-limited reaction) to obtain enhanced performance. Examples of RCUs include one or more chromatographic columns packed with a separation media for the reaction products. The RCU can also include a catalyst for certain equilibrium-limited reactions discussed herein. Both the catalyst (when present) and the separation media can be present in the RCU as a stationary phase. The different reaction products can have different affinities to the stationary phase leading to different migration velocities through the RCU. This leads to the separation of the reaction products, suppression of backward reactions and providing high conversion at the outlet of the RCU.

One example of the RCU suitable for the present disclosure is a simulated-moving bed unit (SMB). The SMB unit provides for a continuous and counter-current operation that combines chemical reaction and separation within one single apparatus. The SMB unit employs multiple fixed-bed columns (or sections of columns), where each fixed bed column contains a catalyst for the equilibrium limited reaction and separation media to separate the FAP and the SDCP reaction products. Different equilibrium limited reactions may require different number and configurations of the multiple fixed-bed columns. For example, from 4 to 24 fixed-bed columns can be used in forming an SMB unit for the equilibrium limited reactions of the present disclosure. The principal inputs and outputs of the SMB unit are the feed, the extract, and the raffinate, where each fixed-bed column includes an input stream and an output stream. Each stream flows into or out of the fixed-bed column of the SMB unit at individual locations and at a particular flow rate which is independently controlled.

During the process, the SMB unit switches input streams and the output streams of liquids from one column to another (or between column sections) to approach the theoretical performance of a true countercurrent solid-liquid flow. Switching the input streams and the output streams from one column to another can be accomplished using valves (e.g., rotary valves or a network of two-position or multi-position valves) which work in conjunction with the inlet and outlet lines of the multiple fixed-bed columns. The fluid-directing device accomplishes moving the locations of the input and output streams by directing the streams to the appropriate inlet or outlet lines of the multiple fixed-bed columns. The liquid flow rates of the feed streams and the step times for the valves of the SMB unit are controlled so that the slow and fast eluting reaction products move in opposite directions relative to the movement or switching of inlet and outlet ports.

The fixed-bed columns of the SMB unit are configured to provide four zones to provide for the equilibrium-limited reaction and to separate the reaction products into two fractions: the extract, which includes the slow-eluting fraction, and the raffinate, which includes the fast-eluting fraction. The four zones of the SMB unit each perform a different function. Zone I contains fixed-bed columns between the eluent inlet (e.g., the SOAR) and the extract outlet; Zone II contains fixed-bed columns between the extract outlet and the feed inlet (e.g., the FODR); Zone III contains fixed-bed columns between the feed inlet (e.g., the FODR) and the raffinate outlet; and Zone IV contains fixed-bed columns between the raffinate outlet and the eluent inlet (e.g., the SOAR). Within the SMB unit, Zones II and III serve to allow the fast and slow components to move farther apart, while Zones I and IV serve to prevent the slow components from falling too far back and the fast components from moving too far forward, respectively.

As discussed herein, the fixed-bed columns of the SMB unit have a catalyst for the equilibrium-limited reaction and separation media to separate the FAP and the SDCP. The catalyst and the separation media can be provided on one structure or can be provided on separate structures in the fixed-bed columns of the SMB unit. The separation media used in the fixed-bed columns of the RCU can be selected so that the reaction components (e.g., the FODR and the FAP are less strongly adsorbed, while the reaction co-product (e.g., the SDCP) is more strongly adsorbed. This allows for less polar reaction component, e.g. the FAP, to be removed from the SMB unit in the raffinate stream, while more polar reaction component, e.g., the SDCP, to be removed from the SMB unit in the extract stream.

The process of the present disclosure is for equilibrium-limited reactions that produce non-aqueous reaction products (e.g., an alcohol), and not for reactions that produce water. Examples of catalysts for equilibrium-limited reactions include, but are not limited to, those for transamination reactions, transamidation reactions, and acylation reactions, such as transesterification reactions and amidation reactions. Examples of catalysts for transesterification reactions include, but are not limited to, to acid, base, metal alkoxide, amine, molecular sieves, and enzyme catalysts as provided in Otera, Junzo; "Transesterification", Chem. Rev., 1993, 93, 1449-1470. Depending upon the composition of the feed, several different catalysts may be combined in order to accomplish the catalysis function.

The process of the present disclosure can use many different types of catalysts and separation media to carry out the equilibrium-limited reaction and separation. It can use either a single solid that can act as both catalyst and separation media, a combination of one or more solid catalysts and separation media, or a homogeneous catalyst with one or more separation media. The separation media can be conventional materials used in adsorption-type processes, including but not limited to polymeric resins, silica, alumina, molecular sieves, activated carbon or other known separation media that can separate at least one of the products of the equilibrium-limited reaction products. The preferred solids are those that can function as both catalyst and separation media in a single solid, such as strong acid ion exchange resins. These include but are not limited to a sulfonated ion exchange resin such as Amberlyst™ 15, Amberlyst™ 70, DOWEX™ MONOSPHERE™ M-31, or other commercially available strong acid polymeric resins. Other solids that can function as both catalyst and separation media in a single solid include a strong base anion exchange resin. For example, the strong base anion exchange resin can be a copolymer matrix with quaternary ammonium functional groups. Examples of such strong base anion exchange resins include DOWEX™ MARATHON A, AMBERLITE™ IRA-900, and AMBERLITE™ IRA-904, among others.

Different equilibrium-limited reactions and separations of products may require different catalyst and separation media combinations and/or different volume ratios of catalyst to separation media. For example, the catalyst and the separation media can be present in the SMB unit in a volume ratio (catalyst:separation media) that ranges from 1:100 to 100:1. The catalyst and the separation media can also be present in the SMB unit in a variety of configurations. For example, when present as separate structures the catalyst and the separation media can be present as a uniform mixture throughout the fixed-bed columns of the SMB unit. Alternatively, the catalyst and the separation media can be present in alternating layers of catalyst and separation media along the fixed-bed columns of the SMB unit. The thicknesses and relative positions of the layers can depend upon the equilibrium limited reaction and the products that need to be separated.

For the process of the present disclosure, the SOAR and the FODR are supplied to the RCU (e.g., the SMB unit) to create a reaction mixture, where the FODR is in a stoichiometric deficit relative to the SOAR for the equilibrium-limited reaction, and where the RCU has separation media to separate the FAP and the SDCP. The process operates continuously, with the SOAR and the FODR being introduced to form the reaction mixture, the equilibrium-limited reaction occurring to form a product mixture that includes the FAP and SDCP, and the FAP and SDCP of the product mixture being separated into the raffinate and the extract. As the FODR is supplied to the RCU at a stoichiometric deficit relative to the SOAR, the SOAR acts as the eluent (also known as desorbent) in both the raffinate and the extract. Suitable examples of supplying the FODR in the stoichiometric deficit relative to the SOAR for the reaction include supplying a stoichiometric ratio of FODR to SOAR (FODR:SOAR) in a range from 1:1.1 to 1:10. In an additional embodiment, supplying the FODR in the stoichiometric deficit relative to the SOAR for the reaction include supplying a stoichiometric ratio of FODR to SOAR (FODR:SOAR) in a range from 1:1.5 to 1:5. In a further embodiment, supplying the FODR in the stoichiometric deficit relative to the SOAR for the reaction include supplying a stoichiometric ratio of FODR to SOAR (FODR:SOAR) in a range from 1:2 to 1:3.

The feed introduced to the SMB unit contains at least one SOAR and at least one FODR, where the SMB unit is operated at a predetermined pressure and a predetermined temperature suitable for the equilibrium limited reaction. Operating conditions will depend upon the catalyst (when present) and the separation media used in the SMB unit. Typical predetermined temperatures for the equilibrium limited reactions in the SMB unit can be from 0° C. to 200° C. Typical predetermined pressures for the equilibrium limited reactions in the SMB unit can be from 101 KPa to 2000 KPa. As appreciated by one skilled in the art, other operating temperatures and pressures are possible depending upon the equilibrium limited reaction. The operating conditions can be set so that the streams of the reactants that form the reaction mixture (e.g., FODR and SOAR) are in the liquid phase, and all components are in the liquid phase.

As discussed herein, the separation media of the RCU allow for separation of the product mixture into a raffinate and an extract. In one embodiment, the raffinate contains at least the FAP, while the extract contains at least the SDCP. As the SOAR is used as the eluent, the raffinate and the extract also contains SOAR (e.g., the raffinate includes SOAR and the FAP, and the extract includes SOAR and the SDCP,). Additionally, residual unreacted FODR may elute from the RCU in either the extract or the raffinate stream. As discussed herein, it is preferable to operate the RCU in such a manner as to separate the residual unreacted FODR into the raffinate stream to avoid the downstream separation of potential azeotropes between the residual unreacted FODR and SDCP. For example, the flow rates in each zone of the SMB (related to both residence time for reaction and separation), the throughput, concentration, temperature can each be modified to achieve proper separation of the correct species into the desired streams. It is also possible that undesirable heavy compounds can be present in the raffinate or the extract, where the heavy compounds were present in the feed or were produced as undesired by-products of the equilibrium limited reaction (e.g., an acylation reaction).

In a preferred embodiment, the RCU is operated in such a manner as to enable high overall conversion of FODR and SOAR to FAP and SDCP without requiring a single high conversion (e.g., greater than 90% conversion of the FODR) through the RCU itself. By not attempting to achieve the highest possible single-pass conversion, but rather a single-pass conversion that is lower than the highest possible value, the overall consumption of SOAR as the elution solvent can be reduced. This can be accomplished through the strategy described herein in which the SOAR fraction from the extract and the recycle fraction from the raffinate are recycled back to the RCU. In addition, the flow rates in each zone of the SMB (related to both residence time for reaction and separation), the throughput, concentration, temperature can each be modified to achieve a desired single-pass conversion that is lower than the highest possible value. The SOAR excess (e.g., the eluent) can be minimized while achieving high overall conversion by providing for economical recovery and recycle of the residual unreacted FODR and SOAR. For example, the optimum single-pass conversion may range from 70 to 99% conversion (on the FODR limiting reagent basis) to enable reduced eluent requirements while achieving high overall conversions approaching 100%.

The raffinate can undergo a separation process to separate the raffinate into a FAP product fraction and a recycle fraction, where the recycle fraction contains the majority of the SOAR, a FAP cut and residual unreacted FODR. The recycle fraction can be returned to the RCU (e.g., the SMB unit), while the FAP cut is collected as a product. In one embodiment, the recycle fraction can be returned to the feed of the RCU. In an additional embodiment, the recycle fraction can be returned to a location within the RCU where the molar compositions of the SOAR, the FODR, and the FAP in the recycle fraction have similar values to the molar concentrations of the SOAR, the FODR and the FAP in the RCU (e.g., a point of similar concentration in the chromatography cycle of the SMB unit).

Suitable separation process for the raffinate include, but are not limited to, distillation processes, as are known, that can form the FAP product fraction and a recycle fraction. Examples of suitable distillation process include continuous distillation processes, including those that use a dividing wall column (DWC). Other separation processes are also possible.

The extract also undergoes a separation process to separate the extract into at least a SOAR fraction and a SDCP fraction. The SOAR fraction can be returned to the feed of the RCU (e.g., the SMB unit), while the SDCP fraction is removed from the process. Suitable separation processes for the extract include, but are not limited to, those discussed herein for the raffinate. As discussed herein, because the equilibrium-limited reactions do not produce water and because the FODR is primarily separated into the raffinate stream, there is less of an opportunity for an azeotrope to form with the FODR and/or the FAP.

As discussed herein, the FODR can react beyond the equilibrium conversion value, as discussed herein, with the SOAR to produce the product mixture. When the FODR does not all react in the RCU, FODR emerges from the RCU. As previously indicated, the residual unreacted FODR is preferably separated into the raffinate stream for easier downstream processing. However, this residual unreacted FODR can also be recovered as a third product from the RCU. In one embodiment, this third product from the RCU can be recovered from the RCU by employing a multi-component SMB separation scheme, where the third product is recovered in a third stream from the RCU. Examples of such schemes for utilizing SMB units, as discussed herein, for separating tertiary reaction mixtures (e.g., raffinate, extract and unreacted FODR) can be found in "Comparison of various ternary simulated moving bed separation schemes by multi-objective optimization" (Agrawal et al., Journal of Chromatography A, 1238 (2012) 105-113), which is incorporated herein by reference in its entirety.

As appreciated by one skilled in the art, the separation of the product mixture into the raffinate and the extract in the RCU might be enhanced by the use of a non-reactive solvent in addition to the SOAR of the mobile phase. Examples of such non-reactive solvents can include, but are not limited to, a ketone. This use of an added mobile phase solvent would be optional, but could be useful to enhance the separation ability of the RCU for the present disclosure.

As discussed herein, the process of the present disclosure can be used for a variety of equilibrium-limited reactions that produce non-aqueous reaction products (e.g., an alcohol), and not for reactions that produce water. An example of such equilibrium-limited reactions includes, but is not limited to, a transesterification reaction. Another example of such equilibrium-limited reactions includes, but is not limited to, a transamination reaction. Yet another example of such equilibrium-limited reactions includes, but is not limited to, an amidation reaction and a transamidation reaction.

For the transesterification reaction, the SOAR can be an organic substrate (OS), while the FODR can be an acylating agent (AA). The process of the present disclosure uses the RCU for the transesterification reaction of the OS with the AA to form the FAP, in this case an acyl-group containing organic compound (AGCOC), and the SDCP, in this case an acyl donor co-product (ADCP). As discussed herein, the RCU allows for the equilibrium-limited reaction of the OS and the AA and the separation of the AGCOC and the ADCP products to drive the conversion of the equilibrium-limited reaction. For example, the process of the present disclosure includes supplying to the RCU the OS and the AA to create the reaction mixture, where the AA is in a stoichiometric deficit relative the OS for the equilibrium limited reaction. The RCU has separation media to separate the AGCOC and the ADCP products into one of two streams: a raffinate and an extract As the AA supplied to the RCU is in a stoichiometric deficit relative the OS, the OS supplied to the RCU is in a stoichiometric excess relative the AA. Due to this stoichiometric excess the OS in addition to being a reactant in the equilibrium limited reaction also acts as the eluent or the desorbent for the extract and the raffinate of the RCU. Likewise, because the AA supplied to the RCU is in the stoichiometric deficit relative the OS, the AA in the RCU reacts beyond the equilibrium conversion value, as discussed herein, to form the AGCOC and the ADCP via the equilibrium limited reaction. The result is the process of the present disclosure greatly simplifies the equilibrium-limited reaction compared to reactive distillation processes, which can have difficulty stripping the ADCP to drive conversion without also taking some of the AA overhead, thus requiring an additional unit operation to separate the resulting azeotropic mixture of AA and ADCP.

In an additional embodiment, it is possible that the OS is in a stoichiometric deficit relative the AA for the equilibrium-limited reaction in the RCU. Such embodiments can address certain equilibrium-limited reactions that have the potential of forming azeotropes of either AGCOC and OS or ADCP and OS reaction products.

For the process of the present disclosure, the OS and the AA are supplied to the RCU (e.g., the SMB unit) as the reaction mixture, where the AA is in a stoichiometric deficit relative the OS for the equilibrium-limited reaction to form the product mixture of the AGCOC and the ADCP. The RCU has separation media, as discussed herein, to separate the AGCOC and the ADCP. The process operates continuously, with the OS and the AA being introduced, the equilibrium-limited reactions occurring and the AGCOC and ADCP products being separated into the raffinate and the extract, respectively. As the AA is supplied to the RCU at a stoichiometric deficit relative the OS to create the reaction mixture, the OS acts as the eluent in both the raffinate and the extract, while the AA reacts beyond the equilibrium conversion value, as discussed herein, to form the product mixture in the RCU.

Suitable examples of supplying the AA in the stoichiometric deficit relative the OS for the reaction include supplying a stoichiometric ratio of AA to OS (AA:OS) in a range from 1:1.1 to 1:10; in a range from 1:1.5 to 1:5; or in a range from 1:2 to 1:3.

The feed introduced to the SMB unit contains at least one OS and at least one AA, where the SMB unit is operated at a pressure and a temperature suitable for the equilibrium limited reaction. Operating conditions will depend upon the catalyst (when present) and the separation media used in the SMB unit. Typical operating temperatures and operating pressures for the equilibrium limited reactions in the SMB unit are provided herein. The operating conditions can be set so that the streams of the reactants (e.g., OS and AA) are in the liquid phase, and all components are in the liquid phase.

For acylation reactions, the OS can include, but are not limited to, a hydroxy containing organic compound (HCOC). HCOCs include those compounds having a free hydroxyl group suitable for undergoing an acylation reaction. Specific examples of the OS and/or the HCOC include, but are not limited to, glycol ethers or combinations thereof. For example, the OS and/or the HCOC is a glycol ether (GE) having the formula:

R'—(OCH$_2$CHR")$_n$—OH where R' is an alkyl group having 1 to 8 carbon atoms or an aryl group having 6 to 11 carbon atoms; R" is hydrogen, methyl, or ethyl; and n is an integer from 1 to 4.

When the OS is a HCOC, the HCOC reacts with the AA to form an organic acetate (OA) and an alcohol co-product (AC) during the acylation reaction. The AA is in the stoichiometric deficit relative the HCOC to react beyond the equilibrium conversion value, as discussed herein, in the RCU that contains a catalyst for the acylation reaction, as discussed herein, and the separation media to separate the OA and the AC. The raffinate separated with the separation media contains at least the OA, and the extract separated with the separation media contains at least the AC.

The AA can be, but is not limited to, an acetate selected from the group consisting of methyl acetate, ethyl acetate (EtAc), propyl acetate, butyl acetate or a combination thereof. The AA can also be selected from the group consisting of a propionate, a benzoate, an adipate, an ester of a glycol ether or a combination thereof. For example, the AA can include an ester of a glycol ether (GE) having the formula:

R'—(OCH$_2$CHR")$_n$—O—R'"

where R' is an alkyl group having 1 to 8 carbon atoms or an aryl group having 6 to 11 carbon atoms; R" is hydrogen, methyl, or ethyl; R'" is hydrogen or an acyl group of the form —C(O)—R"" wherein R"" is an alkyl group having 1 to 3 carbon atoms; and n is an integer from 1 to 4.

In one embodiment, the AA is EtAc, while the OS is GE. In other embodiments, the process of the present disclosure can be used in a transesterification reaction in which the GE is reacted with AA, as provided herein, to form the corresponding glycol ether ester (GEE) plus the corresponding AC (e.g., methanol (MeOH), ethanol (EtOH), propanol (PrOH), or butanol (BuOH)).

As discussed herein, the separation media of the RCU allow for separation of the reaction products into a raffinate stream and an extract stream. The raffinate contains at least the AGCOC, while the extract contains at least the ADCP. As the OS is used as the eluent, the raffinate and the extract also contains OS (e.g., the raffinate includes OS and AGCOC, and the extract includes OS and ADCP, where the raffinate is less polar relative to the extract). Additionally, residual unreacted AA may elute from the RCU in either the extract or the raffinate stream. It is preferable to operate the RCU in such a manner as to separate the residual unreacted AA into the raffinate stream to avoid the downstream separation of potential azeotropes between AA and ADCP. It is also possible that undesirable heavy compounds can be present in the raffinate, where the heavy compounds were present in the feed or were produced as undesired by-products of the equilibrium limited reaction (e.g., an acylation reaction).

The raffinate can undergo a separation process to separate the raffinate into an AGCOC product fraction and a recycle fraction, where the recycle fraction contains the OS, residual unreacted AA, and an AGCOC cut. The recycle fraction can be returned to the RCU (e.g., the SMB unit), while the AGCOC cut is collected as a product. In one embodiment, the recycle fraction can be returned to the feed of the RCU. In an additional embodiment, the recycle fraction can be returned to a location within the RCU where the molar compositions of the OS, AA, and the AGCOC in the recycle fraction have similar values to the molar concentrations of the OS, AA, and the AGCOC in the RCU (e.g., a point of similar concentration in the chromatography cycle of the SMB unit).

Suitable separation process for the raffinate include, but are not limited to, distillation processes, as are known, that can form the AGCOC product fraction and a recycle fraction. Examples of suitable distillation process include continuous distillation processes, including those that use a DWC. Other separation processes are also possible.

The extract also undergoes a separation process to separate the extract into at least an OS fraction and an ADCP fraction. The OS fraction can be returned to the feed of the RCU (e.g., the SMB unit), while the ADCP fraction is removed from the process. Suitable separation processes for the extract include, but are not limited to, those discussed herein for the raffinate. As discussed herein, because the equilibrium limited reactions does not produce water and because the AA is primarily separated into the raffinate stream, there is less of an opportunity for an azeotrope to form with the AA and/or the AGCOC in the extract.

As discussed herein, the AA can react beyond the equilibrium conversion value with the OS. When the AA does not all react in the RCU, AA emerges from the RCU. As previously indicated, the unreacted AA is preferably separated into the raffinate stream for easier downstream processing. However, this unreacted AA can be recovered as a third product from the RCU. In one embodiment, this third product from the RCU can be recovered from the RCU by employing a multi-component SMB separation scheme, as discussed herein.

Embodiments of the present disclosure can also be used to enable enantioselective acylation reactions used to produce enantiomers with enhanced chiral purity. For example, enzyme biocatalysts such as lipases are known to be selective for specific enantiomers and can tolerate non-aqueous liquids, so the enzyme catalyzed acylation reaction can be used to generate compounds with enhanced chiral purity. Non-enzymatic enantioselective catalysts also are known and may be used. Enantioselective amidation and amination reactions also are known. The enantiomers produced by these enantioselective reactions are valuable compounds useful as synthons (synthetic building blocks) for use in the asymmetric (chiral) synthesis of specialty products such as pharmaceuticals, agricultural chemicals, and other biologically-active products. Often these are equilibrium-limited reactions, and the embodiments of the present disclosure can help to drive conversion by providing simultaneous reaction and separation, as discussed herein. Embodiments of the present disclosure may enable enantioselective acylations, and similar reactions, simultaneous production of multiple enantiomer products.

For example, an enantioselective acylation reaction may be carried out such that both a substrate (e.g., the SOAR) and an acyl donor (e.g., the FODR) are chiral compounds (supplied as racemates), so an (R)-enantioselective catalyst can produce up to four enantiomers with enhanced chiral purity: the two (R)-enantiomer reaction products plus the two unreacted (S)-enantiomers. The effective overall reaction can be written:

(R,S)—A+(R,S)-B ⟷ (R)-C+(R)-D+(S)-A+(S)-B    Reaction (1)

Assuming chemical equilibrium limitations can be overcome and all (R)- and (S)-enanatiomers are of commercial interest, the theoretical conversion of reagents to desired products can approach 100 percent. The enantiomers on the right-hand side of Reaction (1) can be separated by chromatography and/or distillation. Similar reactions, such as enantioselective transamidation and enantioselective transamination, are also possible.

One specific example of such an enantioselective acylation reaction to produce multiple enantiomers with enhanced chiral purity can include the (R)-enantioselective reaction of propylene glycol n-butyl ether (PnB) with propylene glycol methyl ether acetate (PMA) to give the (R)-enantiomer reaction products propylene glycol n-butyl ether acetate (PnBA) and propylene glycol methyl ether (PM) plus an unreacted (S)-enantiomers of the two racemic reagents.

(R,S)-PnB+(R,S)-PMA→(R)-PnBA+(R)-PM+(S)-PnB+(S)-PMA (enzyme catalyzed reaction)

This reaction, unlike the other discussed herein, involves the use of both reactants that are supplied in equal stoichiometric amounts and an added mobile phase solvent (e.g., a ketone). Other process configurations and molar ratios are possible to give various reaction mixtures that can be separated by using chromatography and/or distillation methods discussed herein.

For the above reaction, the (R,S)-PnB and the (R,S)-PMA are supplied to the RCU to create the reaction mixture. The RCU has separation media to separate the product mixture of the (R)-PnBA, (R)-PM, (S)-PnB and (S)-PMA into a raffinate and an extract. For example, the extract can include the (R)-PM and (S)-PnB plus the mobile phase, while the raffinate can include the (R)-PnBA and (S)-PMA, plus the mobile phase. As provided for this example, both (R)-enantiomer reagents are supplied to the RCU in stoichiometric ratio and react beyond the equilibrium conversion value. Separation processes, as discussed herein (e.g., distillation) can be used to separate the raffinate into an (S)-PMA fraction and a (R)-PnBA fraction, and to separate the extract into an (R)-PM fraction and a (S)-PnB+mobile phase fraction.

EXAMPLES

The following example is given to illustrate, but not limit, the scope of this disclosure. Unless otherwise indicated, all parts and percentages are by weight. Unless otherwise specified, all instruments and chemicals used are commercially available.

Example 1 (Ex. 1)

Ex. 1 is the transesterification through a single column reactive chromatography test of 1-methoxy-2-propanol (DOWANOL™ PM, The Dow Chemical Company) with ethyl acetate (EMD, HPLC grade, >99.8%) to propylene glycol methyl ether acetate and ethanol.

Pack two stainless steel columns (Supelco, outside diameter 1.27 cm×inner diameter 1.0 cm×length 25 cm) with Amberlyst™ 15 (Sigma Aldrich, hydrogen form, dry) in a slurry with 1-methoxy-2-propanol (Sigma Aldrich, >99.5%). Set up the apparatus in a basic HPLC configuration. Connect the two columns in series and place them into a column oven set at a temperature of 100° C. Use high pressure liquid chromatography (HPLC) pumps to pump the 1-methoxy-2-propanol as the eluent through the columns at a rate of 0.1 mL/min. Maintain the pressure at 100 pounds per square inch gauge (psig) through use of a backpressure regulator. Add the ethyl acetate to the column through a manual valve (Valco 6 port sample injector), using an HPLC pump to directly add a 0.5 ml rectangular pulse onto the column. Collect the effluent from the column at constant time intervals and analyzed by gas chromatography-flame ionized detection (GC-FID).

Comparative Example A (Comp. Ex. A)

Comp. Ex. A repeats the transesterification reaction of Ex. 1, but done in a batch configuration. Load a 250 mL, three-necked round bottom flask with 4.96 g Amberlyst™ 15 resin, 69.8 g of 1-methoxy-2-propanol, and 33.5 g ethyl acetate. Place flask onto heating mantle with a temperature controller and thermocouple. Equip flask with overhead stirrer with Teflon half-moon impeller, Teflon coated thermocouple, water-cooled condenser, and nitrogen pad. Increase agitation to 300 rpm to mix components and set temperature set point to maintain an internal temperature of 75° C. inside the flask. Take samples periodically and analyze by GC-FID.

Figure 1:
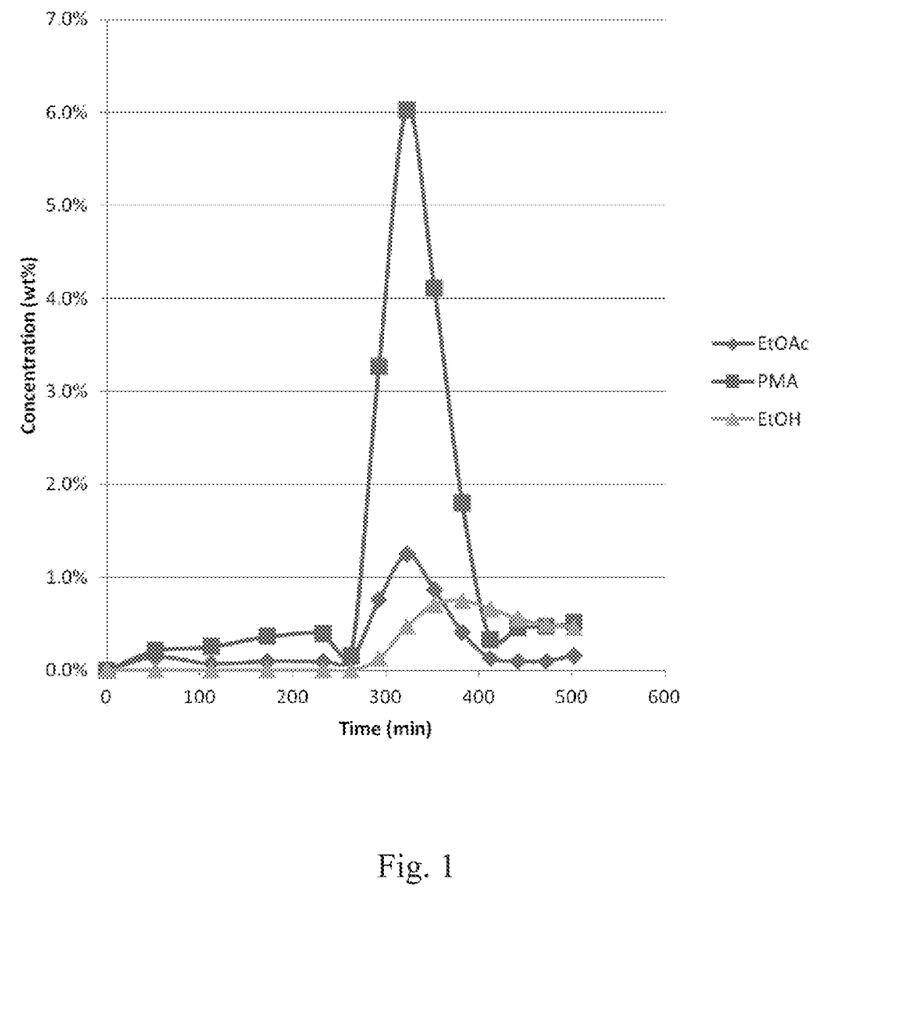
FIG. 1 illustrates ethyl acetate conversion during a trans-esterification reaction catalyzed via strong acid cation exchange resin (column testing) (Ex. 1).
Figure 2:
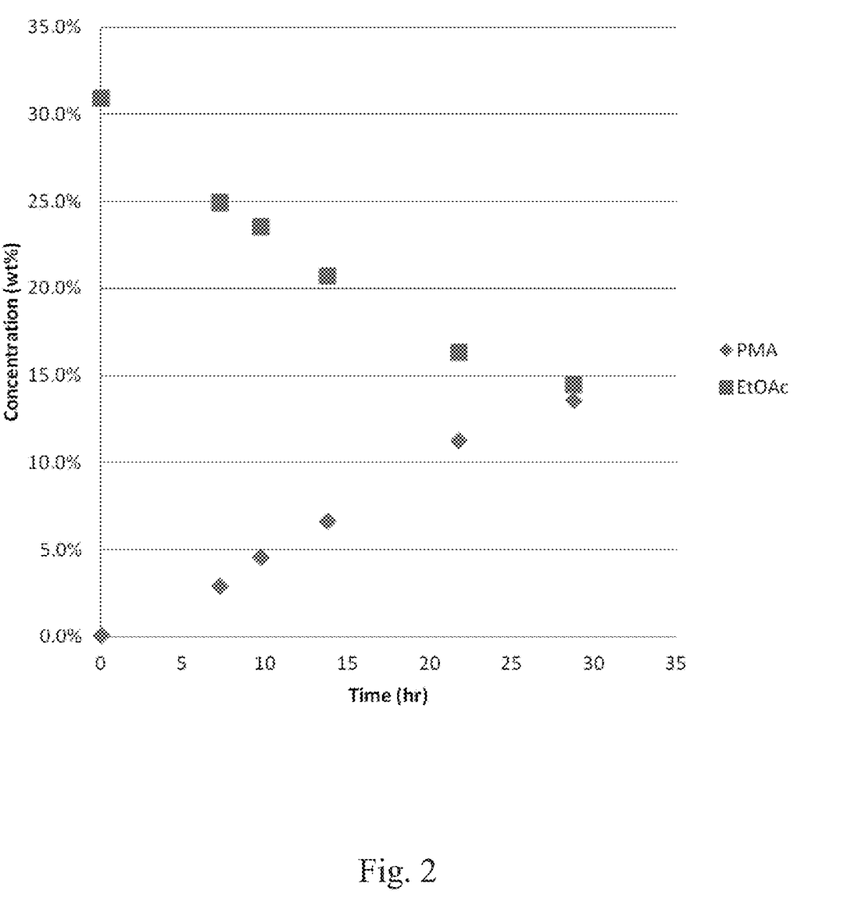
FIG. 2 illustrates ethyl acetate conversion during a trans-esterification reaction catalyzed via strong acid cation exchange resin (batch testing) (Comp. Ex. A).

FIG. 1 illustrates that the separation of the reaction products for Ex. 1 was achieved. FIG. 1 also illustrates that for Ex. 1 the conversion of ethyl acetate exceeded the equilibrium limit in achieving a conversion of approximately 73 weight percent (wt. %) based on the reaction products (estimated from calculations using the trapezoidal rule). This is a significant improvement from the batch experiment of Comp. Ex. A, where FIG. 2 illustrates that only 53 wt. % (based on the reaction products) of ethyl acetate converted after 28 hours. This result is believed to be due to achieving reaction equilibrium for the transesterification reaction.

Example 2 (Ex. 2)

Ex. 2 is the transesterification through a single column reactive chromatography test of 1-methoxy-2-propanol (PM, Alfa Aesar, 99+%) with ethyl acetate (EMD, HPLC grade, ≥99.8%) to propylene glycol methyl ether acetate and ethanol with a strong base anion exchange resin.

Prepare the 1-methoxy-2-propanol by drying with 3Å molecular sieves. Dehydrate DOWEX™ MARATHON A (The Dow Chemical Company) anion exchange resin by packing the wet adsorbent into one stainless steel column (Knauer, inner diameter 0.8 centimeters, length 0.25 meters) and then flowing 12 bed volumes of the dried 1-methoxy-2-propanol through the column with a high pressure liquid chromatography (HPLC) pump set to a flow rate of 0.1 bed volume per minute. Place the column into a column oven set at a temperature of 40° C. and continue to pump the 1-methoxy-2-propanol as the eluent through the column at a rate of 0.1 bed volume per minute. Add the ethyl acetate to the column through a manual injection valve (Rheodyne manual injector, RH-7725I), using an HPLC pump to directly add a 1.0 ml rectangular pulse onto the column. Collect the effluent from the column at constant time intervals and analyze by gas chromatography-flame ionized detection (GC-FID).

Comparative Example B (Comp. Ex. B)

Comp. Ex. B repeats the transesterification reaction of Ex. 2, but done in a batch configuration. Prepare the 1-methoxy-2-propanol by drying with 3Å molecular sieves. Dehydrate DOWEX™ MARATHON A (The Dow Chemical Company) anion exchange resin by packing the wet adsorbent into a glass column (inside diameter 1.5 cm and length 22.6 cm) and then flowing 8.0 bed volumes of the dried 1-methoxy-2-propanol through the column with an HPLC pump set to a flow rate of 0.0675 bed volumes per minute. Remove the dehydrated resin (8.75 g) and load it with 1-methoxy-2-propanol (100 mL) into a four-necked spherical glass flask of 500 mL capacity fitted with a coil condenser to prevent any loss of products. Control the temperature within ±0.1K by a PID-temperature controller in a water bath and equip flask with overhead stirrer. Mix components and set temperature set point to maintain an internal temperature of 40° C. inside the flask. After the mixture reaches the desired temperature, add preheated ethyl acetate (100 mL) to the flask. Take 0.1 mL samples periodically and analyze by GC-FID.

Figure 3:
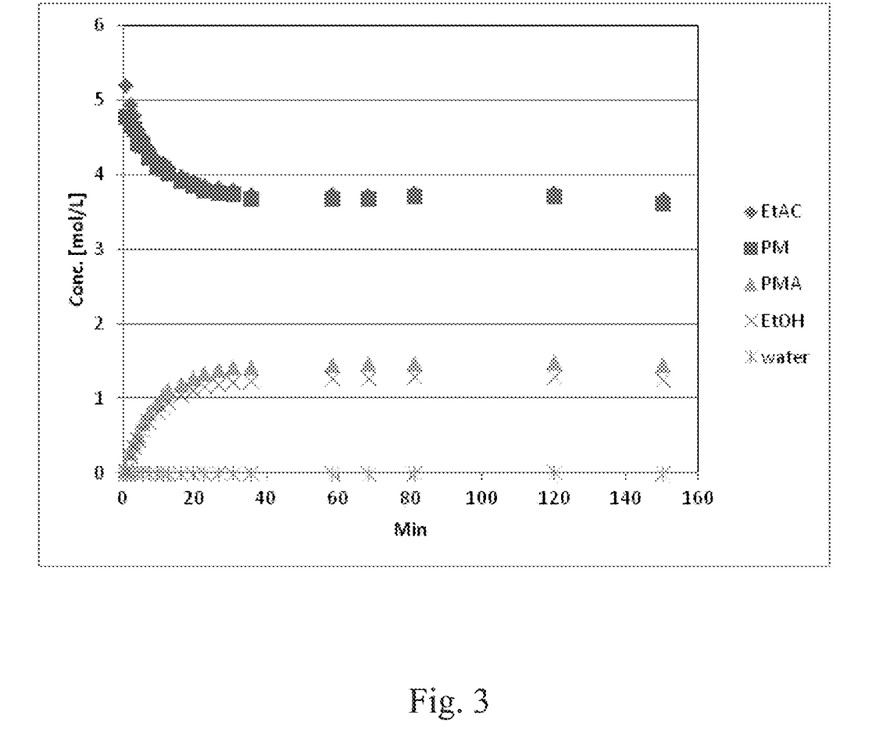
FIG. 3 illustrates ethyl acetate conversion during a trans-esterification reaction catalyzed via strong base anion exchange resin (batch testing) (Comp. Ex. B)

Table 1 illustrates that for Ex. 2 the conversion of ethyl acetate exceeded the equilibrium limit in achieving a conversion of approximately 78.7 weight percent (wt. %) based on the reaction products (estimated from calculations using the trapezoidal rule). This is a significant improvement from the batch experiment of Comp. Ex. B, where FIG. 3 illustrates that only 30.3 wt. % (based on the reaction products) of ethyl acetate converted after 40 minutes. This result is believed to be due to achieving reaction equilibrium for the transesterification reaction.

TABLE 1

| Volume of EtAc injected (mL) | Amount of EtAc injected (mol) | Amount of EtAc collected (mol) | Amount of EtAc reacted (mol) | PMA formed (mol) | Ratio of PMA formed to EtAc reacted | Conversion of EtAc (wt. %) |
| --- | --- | --- | --- | --- | --- | --- |
| 1.00 | 0.0102 | 0.00217 | 0.00080 | 0.00864 | 1.079 | 78.7 |

We claim:

1. A process for an equilibrium-limited reaction of an acylating agent with a hydroxy containing organic compound (HCOC) to form an organic ester and an alcohol co-product (AC) different than the HCOC, where the equilibrium-limited reaction is a reversible reaction having an equilibrium conversion value ($X_e$) for a predetermined temperature, the process comprising:
supplying the acylating agent and the HCOC to a reactive chromatography unit (RCU) to create a reaction mixture, where the acylating agent is in a stoichiometric deficit relative to the HCOC for the equilibrium-limited reaction, and where the RCU has a catalyst for the equilibrium-limited reaction and separation media to separate the organic ester from the AC;
reacting at the predetermined temperature the acylating agent in the stoichiometric deficit relative to the HCOC in the RCU to form a product mixture comprising the organic ester and the AC via the equilibrium limited reaction; and
separating the product mixture with the separation media into a raffinate that includes the organic ester and an extract that contains the AC, where separating the product mixture produces a conversion value for the equilibrium limited reaction that is greater than the equilibrium conversion value for the predetermined temperature.

2. The process of claim 1, where the HCOC acts as an eluent in both the raffinate and the extract.

3. The process of claim 2, where the raffinate includes the HCOC, residual unreacted acylating agent, and the organic ester, and the process further includes:
separating the raffinate into an organic ester product fraction and a recycle fraction, where the recycle fraction contains the HCOC, residual unreacted acylating agent, and an organic ester cut; and
returning the recycle fraction to the RCU.

4. The process of claim 2, where the extract includes the HCOC and the AC, and the process further includes:
separating the extract into at least a HCOC fraction and a AC fraction; and
returning the HCOC fraction to the RCU.

5. The process of claim 1, where reacting the acylating agent in the stoichiometric deficit relative to the HCOC provides a single pass conversion of the acylating agent of 70 percent (%) to 99%.

6. The process of claim 1, where the RCU includes a strong acid ion exchange resin to both catalyze the equilibrium-limited reaction and to separate the raffinate and the extract.

7. The process of claim 6, where the strong acid ion exchange resin is a sulfonated ion exchange resin.

8. The process of claim 1, where the RCU includes a strong base anion exchange resin to both catalyze the equilibrium-limited reaction and to separate the raffinate and the extract.

9. The process of claim 8, where the strong base anion exchange resin is a copolymer matrix with quaternary ammonium functional groups.

10. The process of claim 1, where the acylating agent is an acetate, or an ester selected from the group consisting of a propionate, a benzoate, an adipate, an ester of a glycol ether or a combination thereof.

11. The process of claim 10, where the acetate is selected from the group consisting of methyl acetate, ethyl acetate, propyl acetate, butyl acetate or a combination thereof.

12. The process of claim 1, where the HCOC is a glycol ether (GE) having the formula:

R'—(OCH$_2$CHR")$_n$—OH where R' is an alkyl group having 1 to 8 carbon atoms or an aryl group having 6 to 11 carbon atoms; R" is hydrogen, methyl, or ethyl; and n is an integer from 1 to 4.

13. The process of claim any one of claims 11-12, where the acylating agent is ethyl acetate.

14. The process of claim 1, where the RCU is a simulated-moving bed unit.

* * * * *